United States Patent [19]
Mann et al.

[11] Patent Number: 5,304,347
[45] Date of Patent: Apr. 19, 1994

[54] LIQUID TRANSFER DEVICE FOR AN ANALYSIS UNIT

[75] Inventors: Karl-Heinz Mann, Weilheim; Leonhard Geissler; Andrea Sigl, both of Tutzing, all of Fed. Rep. of Germany

[73] Assignee: Boehringer Mannheim GmbH, Mannheim, Fed. Rep. of Germany

[21] Appl. No.: 14,271

[22] Filed: Feb. 5, 1993

[30] Foreign Application Priority Data

Feb. 8, 1992 [DE] Fed. Rep. of Germany ....... 4203638

[51] Int. Cl.$^5$ ............................................. G01F 23/24
[52] U.S. Cl. ........................................ 422/67; 422/50; 422/63; 422/64; 422/65; 422/66; 422/100; 422/102; 73/61.63
[58] Field of Search ................... 422/50, 63, 65, 66, 422/67, 102, 64, 100; 73/61.63; 137/88, 93

[56] References Cited

U.S. PATENT DOCUMENTS

| | | |
|---|---|---|
| 3,754,444 | 8/1973 | Ure et al. . |
| 4,338,279 | 7/1982 | Orimo et al. ............... 422/64 |
| 4,451,433 | 5/1984 | Yamashita et al. .......... 422/63 |
| 4,543,238 | 9/1985 | Mimura et al. ............. 422/63 |
| 4,647,432 | 3/1987 | Wakatake .................. 422/64 |
| 4,736,638 | 4/1988 | Okawa et al. . |
| 4,818,492 | 4/1989 | Shimizu . |
| 4,939,925 | 7/1990 | Sakuma et al. ........... 73/61.63 |
| 5,004,582 | 4/1991 | Miyata et al. ............. 422/56 |
| 5,045,286 | 9/1991 | Kitajima et al. ........... 422/100 |
| 5,049,826 | 9/1991 | Sasao ...................... 422/106 |
| 5,104,621 | 4/1992 | Pfast et al. ............... 422/67 |
| 5,147,610 | 9/1992 | Watanabe et al. .......... 422/64 |
| 5,178,835 | 1/1993 | Uekusa et al. ............. 422/66 |

FOREIGN PATENT DOCUMENTS

| | | |
|---|---|---|
| 0164679 | 12/1985 | European Pat. Off. . |
| 0280965 | 9/1988 | European Pat. Off. . |
| 0355791 | 2/1990 | European Pat. Off. . |
| 3248449 | 7/1983 | Fed. Rep. of Germany . |
| 3905622 | 8/1989 | Fed. Rep. of Germany . |
| 3909515 | 10/1989 | Fed. Rep. of Germany . |

OTHER PUBLICATIONS

Abstract of DE 32 48 449; Derwent-Recherche.

*Primary Examiner*—James C. Housel
*Assistant Examiner*—Harold Y. Pyon
*Attorney, Agent, or Firm*—Nikaido, Marmelstein, Murray & Oram

[57] ABSTRACT

Liquid transfer device for an analysis unit with a capacitive liquid level detector (10) for detecting the dipping of a liquid transfer needle (5) into an analysis liquid (4). More reliable operation, in particular a better ratio between useful signal and noise signals, is achieved by the fact that the liquid transfer needle (5) is part of a coaxial electrode arrangement (11). The coaxial electrode arrangement includes, in addition to the liquid transfer needle (5), at least one coaxial electrode (12, 13) surrounding the needle and insulating from it and a detection circuit (17). This detection circuit detects a change in capacitance between the electrodes (5, 13) of the liquid level detector (10), and includes an isolation amplifier circuit (23) to whose input (23a) and output (23b) two adjacent electrodes (5, 12) of the coaxial electrode arrangement (11) are connected as signal electrode and compensating electrode. As a result of this structure, no voltage difference occurs between the signal electrode and the compensating electrode.

24 Claims, 2 Drawing Sheets

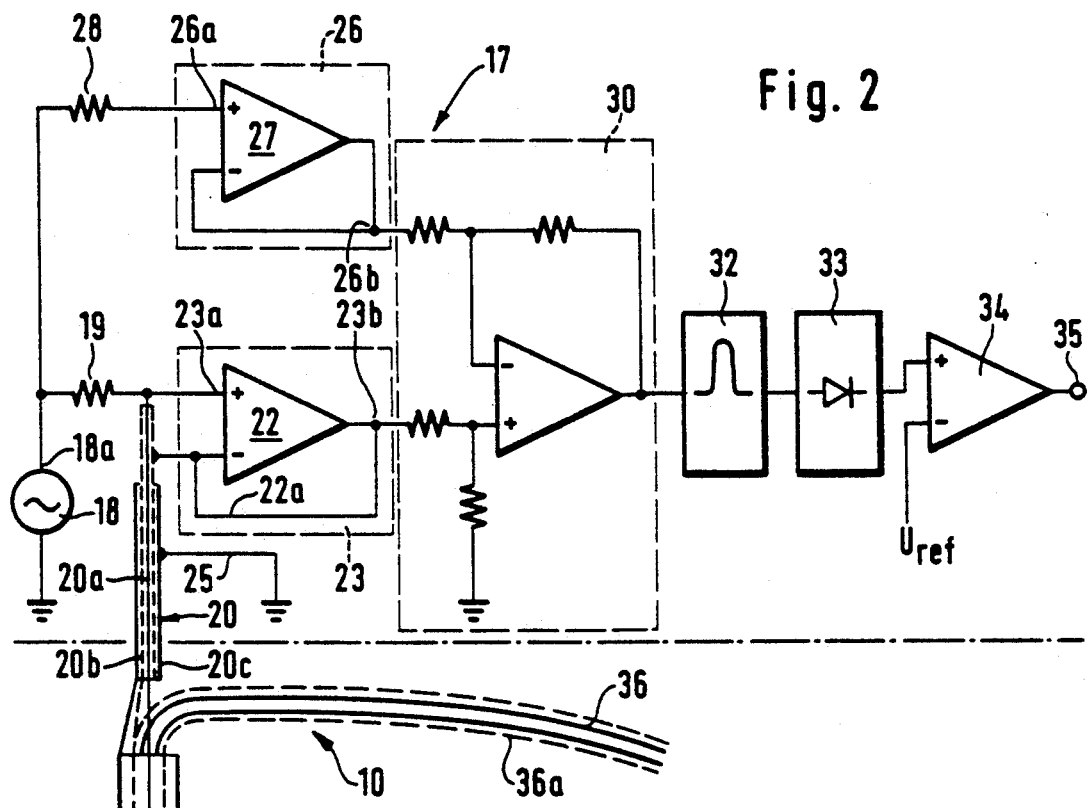
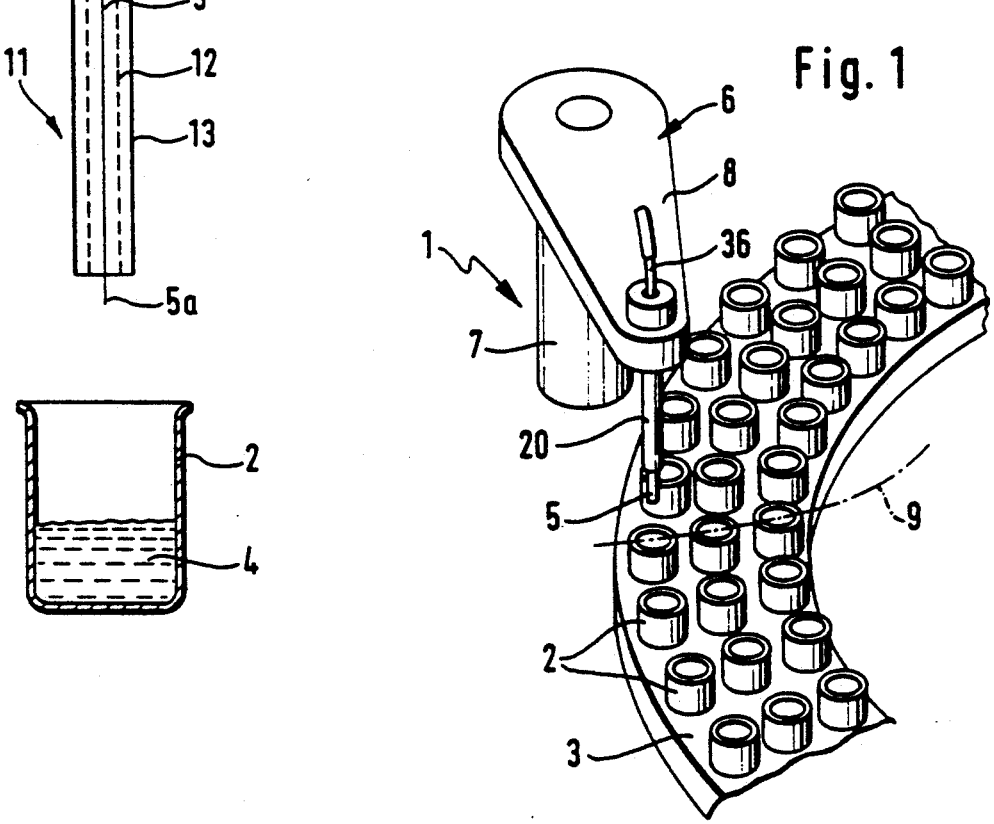

LIQUID TRANSFER DEVICE FOR AN ANALYSIS UNIT

BACKGROUND OF THE INVENTION

1. Field of the Invention

The invention relates to a liquid transfer device for a fluid analysis unit. The liquid transfer device has a liquid transfer needle and a capacitive liquid level detector, for detecting the submersion or dipping of the liquid transfer needle into an analysis liquid contained in a vessel. The liquid level detector includes two electrodes and a detection circuit with an a.c. voltage source for detecting a change in capacitance between the electrodes.

2. Description of the Related Art

In analysis units of the type necessary for the analysis of body fluids such as blood, liquid transfer devices are required in order to transfer analysis liquids, such as liquid samples or reagents. Common liquid transfer devices are, for example, pipettes, which are used for removing samples or reagents from a first vessel and ejecting them into a second vessel. Another common liquid transfer device is a dispenser in which the liquid transfer needle is connected via a hose to a greater stock of the liquid, which may be ejected through the needles by means of a pump device. Dispensers usually also perform the function as a pipette. A liquid transfer device for the purpose of the present invention is essentially any device or structure which in an analysis unit serves to dip into an analysis liquid in order to make possible some liquid transfer steps (intaking and/or ejection of liquid) by means of the liquid transfer needle. The liquid transfer needle is a hollow needle which usually consists of a thin tube of metal or plastic. It will be referred to herein, for the sake of simplicity, as the "needle".

If the needle is dipped or submerged deep into the analysis liquid, a relatively large amount of excess liquid remains undesirably suspended in and around the needle. The amount of liquid transfer can thereby be inaccurate, and during the next dip of the needle, the excess liquid contaminates the remaining analysis liquid (so-called "carry over") In order to better monitor the dipping depth, liquid transfer devices are provided with a sensor device for detecting the dipping of the needle into the analysis liquid, which is usually referred to as a liquid level detector or LLD. The liquid level detector is connected to a vertical drive by means of which the needle is dipped into the analysis liquid, in order to arrest the dipping movement when the tip of the needle is dipped in the analysis liquid by a few millimeters. The vertical position of the needle acts as a measure of the level of the liquid in the respective vessel. Consequently, the liquid level detector makes it possible to monitor the amount of liquid present in the respective vessel, in order to give a signal when the stock of a reagent liquid is depleted and the reagent bottle therefore has to be replaced.

A commonly used construction principle for liquid level detectors is based on measuring the electrical resistance between the needle and an electrode attached to the tip of the needle. Needle and electrode are insulated electrically from one another, so that the electrical resistance between them in the dry state is very high. Upon dipping the needle and the electrode into a sample liquid, the sample liquid closes the circuit so that the electrical resistance changes suddenly. The resulting signal can be detected reliably with simple electronic means. It is regarded as a major disadvantage of this principle, however, that an electrode must be dipped into the liquid in addition to the needle, which increases the amount of excess liquid which unavoidably remains suspended thereupon. The previously mentioned problems with regard to carryover and reduced accuracy are therefore further exacerbated.

Superior detectors for this purpose are liquid level detectors in which a change in the electrical capacitance between two sensor electrodes is recorded as a signal for detecting the dipping of the needle into the liquid. The signal is recorded by an electronic detection circuit coupled to the sensor electrodes, which includes an a.c. voltage source. The first electrode is usually the needle, which can consist of metal or an electrically conductive (metallized) plastic material; the hot pole of the a.c. voltage source is connected thereto, thereby forming a signal electrode. The counter electrode, which is usually connected to earth potential or ground, can be arranged on the outside of the liquid vessel, such as below the bottom and partially around the side walls of the vessel. It is usually an integral part of the vessel support. Upon dipping the needle tip into the liquid, the capacitance between the signal electrode and the counter electrode changes on the basis of the electrical conductivity and the dielectric properties of the liquid.

Liquid level detectors of the kind are described in EP-A No. 0 164 679, U.S. Pat. No. 4,818,492, and EP-A No. 0 355 791, which are hereby incorporated by reference. These printed publications contain more detailed explanations, to which reference will be made here.

A basic problem with these capacitive liquid level detectors exists in the fact that the change in capacitance upon the dipping into the liquid is very small in comparison with the other capacitances which are inherently present, such as "noise capacitances" from, for example, the connecting cable and the amplifier input. The ratio of the useful signal to the noise signals is consequently highly unsatisfactory. Particularly problematic is the fact that some of the noise capacitances are not constant, but change relatively rapidly with time. This is particularly applicable to capacitive interference, which is caused by the movement of objects, such as component parts of the automatic analysis unit, and hands or other parts of the body of the operating personnel. On a fully automatic analysis unit which has numerous moving parts, such interference is impossible to avoid in practice.

In EP-A No. 0 355 791, a specific problem of this kind (noise caused by a membrane sealing the vessel) is corrected by the fact that a reference signal is fixed upon the contacting of the membrane, and during the further downward movement of the needle the difference relative to the fixed reference signal is detected. However, this method is directed towards this specific application. Noise capacitances which change between the fixing of the reference signal and the detection of the liquid surface can often lead to faulty detection.

In the case of the liquid level detector described in the U.S. Pat. No. 4,818,492, the noise capacitance of the leads is compensated passively by means of a bridge circuit. Other capacitive noise is not thereby eliminated, however, and can similarly cause faulty detection with this type of detector.

SUMMARY OF THE INVENTION

An object of the invention is to provide for liquid transfer devices of analysis units a liquid level detector with improved noise reduction, in order to allow more reliable operation and detection.

This object is achieved in the case of a liquid transfer device of the kind which measure electrical capacitance, as described earlier at the outset by utilizing a liquid transfer needle as part of a coaxial electrode arrangement, in which the coaxial electrode arrangement includes the liquid transfer needle and at least one coaxial electrode which surrounds the liquid transfer needle. The detection circuit comprises an isolation amplifier circuit having two adjacent electrodes of the coaxial electrode arrangement connected to the input and output thereof as signal electrode and compensating electrode. The output signal of the isolation amplifier circuit matches the input signal in level and phase. Consequently, no voltage difference occurs between the signal electrode and the compensating electrode.

At least one coaxial electrode almost completely surrounds the liquid transfer needle with a metallically conductive surface. In the radial direction, the needle is enveloped over its whole periphery. In the axial direction, the coaxial electrode extends over the entire length of the needle with the exception of the needle tip, which projects a short distance out of the coaxial electrode.

Any circuit can be used as the isolation amplifier circuit, as long as the output signal coincides with the input signal in phase and level while the output-side internal resistance is lower than the input resistance.

The needle preferably is formed throughout of a metallically conductive material, but a tube of plastic material, into which a metallic conductor is incorporated over its whole length, may also be used.

In the present invention, no voltage difference may occur between the signal electrode and the compensating electrode. Therefore, the existing capacitance is not effective; it is actively compensated. The useful capacitance is therefore detected with very little interfering capacitances. Essentially, only the capacitance in the region of the tip of the needle is detected.

The active compensation makes it possible, according to a preferred embodiment, to provide an additional screening electrode without affecting the useful signal. This screening electrode surrounds the coaxial electrode arrangement as the outermost electrode, and is connected to a constant potential such as ground potential. The screening electrode can also act as the counter electrode of the capacitance measuring arrangement. A counter electrode fixed below the bottom or on the side wall of the vessel then becomes unnecessary. Upon dipping the needle into the liquid, a change in capacitance takes place due to an enlargement of the active capacitor area in the direct vicinity of the needle. Noise caused by the environment, such as by moved objects, is thereby largely eliminated. The radiation of the high-frequency signal of the a.c. voltage source is very low. Although in this embodiment the capacitively active area is very small and the absolute value of the capacitive change therefore relatively low, a surprisingly good signal-to-noise ratio is obtained due to the fact that the suppression of virtually all noise signals is achieved in the context of the invention.

The electric conductors or lines with which the electrodes are connected to the detection circuit are disposed so that interfering line capacitances are avoided and/or compensated. Screened coaxial lines are preferably used, the conductors of the coaxial line arrangement being connected to the needle and to the coaxial electrodes in the order corresponding to the coaxial electrode arrangement.

BRIEF DESCRIPTION OF THE DRAWINGS

The invention will be explained in detail below with reference to the following detailed description of an exemplifying embodiment when considered in conjunction with the accompanying drawings, wherein:

FIG. 1 is a perspective view of a liquid transfer device according to the present invention;

FIG. 2 is a view in highly diagrammatic form of a coaxial electrode arrangement in conjunction with a wiring diagram of the detection circuit;

DESCRIPTION OF THE PREFERRED EMBODIMENTS

The liquid transfer device 1 shown in FIG. 1 is for removing an analysis liquid out of one of the vessels 2 and transferring it into another vessel. The vessels 2 are located on rotor 3 or another suitable movable vessel support. Automatic analysis units generally include a plurality of vessel supports.

Figure 3:
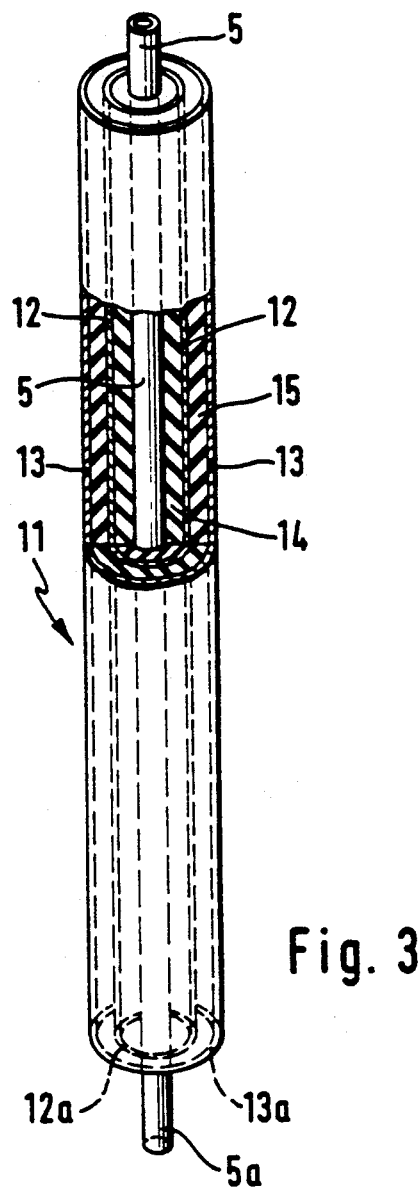
FIG. 3 is a partially cut-away perspective view of a coaxial electrode arrangement.

A liquid transfer needle 5 is fixed to a needle moving unit 6; needle moving unit 6 includes a vertical column 7 movable upwards and downwards by means of a vertical drive (not shown) and a swivel arm 8. The needle 5 may thereby be brought into various positions on the swivel circle 9 and be lowered into one of the vessels 2. Liquid transfer devices of this kind are known in various embodiments. Suitable drive mechanisms are known in the art, such as that shown in EP-A No. 0 408 804, which is hereby incorporated by reference. The liquid transfer needle 5 is part of a coaxial electrode arrangement 11, which is shown in FIG. 2 in a highly diagrammatic cross-sectional view and in FIG. 3 in perspective.

The liquid transfer needle 5 forms the innermost electrode of the coaxial electrode arrangement 11 of a liquid level detector designated overall as 10. It is surrounded by a first coaxial electrode 12 and a second coaxial electrode 13, which are in each case insulated electrically from the needle and from each other by a dielectric 14 or 15. The coaxial electrodes 12, 13 consist of a metallically conductive material, for example, a thin metal foil, and surround the needle 5 completely with the exception of the tip 5a, which projects a short distance therefrom (usually less than 1 cm) in the axial direction.

The detection circuit 17 of the liquid level detector 10, shown in FIG. 2, includes an a.c. voltage source 18 whose hot pole 18a is connected to the needle 5 via a load resistor 19 and the innermost conductor 20a of a coaxial cable 20. The needle 5 is also connected to the non-inverting input 23a of an operational amplifier 22 whose output is connected via the line 22a to its inverting input. This is a common embodiment of an isolation amplifier circuit 23. The output 23b of the isolation amplifier circuit 23 is connected via a first (inner)

screened conductor 20b of the coaxial cable 20 to the first coaxial electrode 12.

The output signal of the isolation amplifier circuit 23 matches the input signal in level and phase. Consequently, no voltage difference occurs between the needle 6 and the compensating electrode 12 Due to the active compensation, the capacitance present in the coaxial cable 20 and the coaxial electrode arrangement 11 is not effective.

As a result of this active compensation the capacitance of the coaxial electrode arrangement 11, including the leads (coaxial cable 20), is formed predominantly by the stray field between the tip 5a of the needle 5 and the electrode 13; this stray field forms the useful capacitance. This capacitance forms a voltage divider with the resistor 19. The greater the capacitance becomes, the smaller the capacitive resistance of the useful capacitance becomes. A change in voltage at the input 23a of the isolation amplifier circuit 23 therefore occurs, which may be measured as the useful signal.

The frequency of the a.c. voltage source 18 and the resistance of the load resistor 19 are optimized such that for a given useful capacitance, as great a voltage difference as possible is obtained. Since the alternating-current resistance of a capacitor is inversely proportional to the frequency, the a.c. voltage frequency should be set relatively high. A frequency of about 50 kHz has proven suitable. Although a higher frequency would further improve the useful signal, it would on the other hand cause problems with interfering radiation and require relatively expensive components.

The value of the load resistor 19 preferably lies in the order of magnitude of the alternating-current resistance of the useful capacitance at the selected frequency.

In the preferred embodiment shown, the second, outer coaxial electrode 13 lies at a constant potential, it being connected to earth (line 25) via the second, outer screened line 20c of the coaxial cable 20. The outer coaxial electrode 13 thus serves as a screening electrode for screening the incoming interference of external noise fields and in particular for screening in an outward direction noise caused by the high-frequency signal applied to the needle 5 and the compensating electrode 12. This screening is possible without interference to the useful signal because of the active compensation between electrodes 5 and 12.

It is particularly advantageous for the screening electrode 13 in the preferred embodiment to also act as the counter electrode of the useful capacitance. As long as the tip 5a of the liquid transfer needle 5 (as shown in FIG. 2) does not dip into the analysis liquid 4, the effective useful capacitance is only due to the stray field in the narrowly confined region of the tip 5a between the tip 5a and the lower part of the second coaxial electrode 13. When the tip 5a dips into the liquid 4, the electrical conductivity always present in the case of analysis liquids results in the liquid surface acting as an "additional capacitor plate". The dipping therefore leads to an effective enlargement of the capacitor area and hence to an enlargement of the useful capacitance. This rise in capacitance is smaller than in the case of the previously known capacitive liquid level detectors which would have a counter electrode fitted to the underside or in the region of the wall of the vessel 2.

The present invention makes it possible to detect this small change with exceptional reliability, because of the considerably improved ratio of the useful signal and the noise signal. It is a particular advantage that interference caused by the environment, such as moved objects, is largely eliminated.

It is also possible to locate the counter electrode of the liquid level detector outside the coaxial electrode arrangement 11, for example below the bottom of the vessel 4. This may also be combined with a coaxial screening electrode. The effectiveness of the coaxial screening electrode as a counter electrode in comparison with an additionally present special counter electrode (below the vessel 4) is dependent upon the distance between the part of the liquid transfer needle 5 which projects out of the compensating electrode 12 and the lower end 13a of the second coaxial electrode (screening electrode) 13. In other words, the gap between the lower end 12a of the first coaxial electrode (compensating electrode) 12 and the lower end 13a of the screening electrode 13 is critical for the effectiveness of the screening electrode 13 as the counter electrode of the liquid level detector 10. In the preferred embodiment shown, ends 12a, 13a are situated at the same level, at the smallest possible distance from one another. The capacitance is, in that case, governed by the stray field between the tip 5a and the screening electrode 13 even if an additional electrode lying at constant potential (such as an earthed support) is provided in the vicinity of the vessel 4. Electrode 13 acts as a counter electrode. This is also still the case if the lower end 13a of the screening electrode 13 is positioned slightly higher than the lower end 12a of the compensating electrode 12. The gap between both ends in the vertical direction should, however, not be more than 15 mm, preferably not more than a maximum of 10 mm.

In the preferred embodiment shown in FIG. 2, the detection circuit comprises a second identical isolation amplifier circuit 26 which is constructed with the aid of a second operational amplifier 27. The signal of the a.c. voltage source 18 is connected to the input 26a of the isolation amplifier circuit 26 via a load resistor 28. The isolation amplifier circuits 23 and 26 should be constructed as identical as possible and are preferably integrated monolithically on a semiconductor chip. The load resistor 28 of the second isolation amplifier circuit should also coincide with the load resistor 19.

The outputs 23b, 26b of the two isolation amplifier circuits 23, 26 are connected to a differential amplifier 30 constructed in the usual manner. The output signal of the differential amplifier 30 is consequently proportional to the difference of the output signals of the isolation amplifier circuits 23, 26. In this way, a passive compensation of the input capacitances of the operational amplifiers 22, 27, and any array capacitances operating in this region, is obtained. The quality of the compensation is dependent on the capacitances of the two signal processing sections 19, 23 and 28, 26 being well matched and as small as possible. This is ensured very effectively in the case of the dual operational amplifiers preferably used, so that the signal applied at the output of the differential amplifier 30 depends mainly on the useful capacitance in the region of the needle tip 5a.

The a.c. voltage signal at the output of the differential amplifier 30 is filtered with a narrow-band filter 32 and converted by means of a rectifier with integrator 33 into a d.c. voltage signal. This d.c. signal is a direct measure of the useful capacitance in the region of the needle tip 5a. This d.c. voltage signal is compared by means of comparator 34 with a comparison voltage $U_{ref}$ which is set to a mean value between the signal in the non-dipped-in state and the signal in the dipped-in state. At the digital output 35 of the detection circuit, a digital logic signal (logic 1 or logic 0) is then available, which is used in the usual manner for controlling the vertical drive of the needle moving unit 6.

In the preferred embodiment, the liquid transfer device 1 is constructed as a dispenser, and a hose 36 connects needle 5 to a liquid supply such as a buffer liquid, which is required in fairly large quantities. In this case, the hose 36 should, as shown in FIG. 2, be provided with screening 36a lying at the compensating potential of the compensating electrode 12. In certain cases, it is also possible to incorporate hose 36 into a coaxial cable-tubing, which fulfills the hydraulic function of sucking in and ejecting liquid, and the electrical function of electrically conducting the coaxial electrode arrangement 11 to the detection circuit 17. In this case, the hose is surrounded by a plurality of screened conductors coaxial to one another, which are connected to the coaxial electrodes in a corresponding manner.

In the embodiment shown in FIG. 2, needle 5 is connected to hot pole 18a of a.c. voltage source 18, and thus forms the signal electrode. This is advantageous in most cases. It is also possible, however, to connect needle 5 to a constant potential, which may be advantageous if the conductive liquid 4 is in contact with other components such as hoses or bottles which also lie at a constant potential, such as earth potential. In this case, the coaxial electrode arrangement includes, in addition to the needle, at least three and preferably four coaxial electrodes, the first (innermost) and third coaxial electrodes being connected to the output of the isolation amplifier circuit, while the second coaxial electrode (in between the first and third) is connected to the input of the isolation amplifier circuit. The second coaxial electrode is connected to the hot pole of the a.c. voltage source, thereby forming the signal electrode. The capacitances on either side are compensated by the adjacent compensating electrodes. In this case, the signal electrode and the two compensating electrodes are preferably surrounded by an additional outer coaxial electrode as a screening electrode, which lies at constant potential. The counter electrode for measuring the capacitance is formed by the needle, which preferably lies at the same constant potential.

Figure 4:
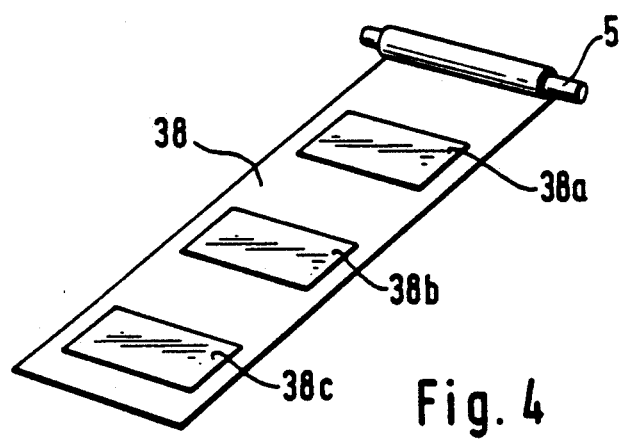
FIG. 4 is a diagrammatic perspective view illustrating a preferred method of producing a coaxial electrode arrangement.

FIG. 4 illustrates a preferred procedure for producing the coaxial electrode arrangement. There is wound around the needle 5 a plastic foil 38, which includes a plurality of metallized regions 38a to 38c which, in the wound-on state, form the coaxial electrodes. The dimensions of the metallized regions and their spacings are proportioned so that the coaxial electrodes formed by the metallized regions 38a to 38c in each case completely surround the needle 5, but in the wound-on state are insulated from one another by plastic foil 38. This procedure makes it possible to produce a coaxial electrode arrangement with good mechanical properties for the invention, in a simple manner.

Figure 5:
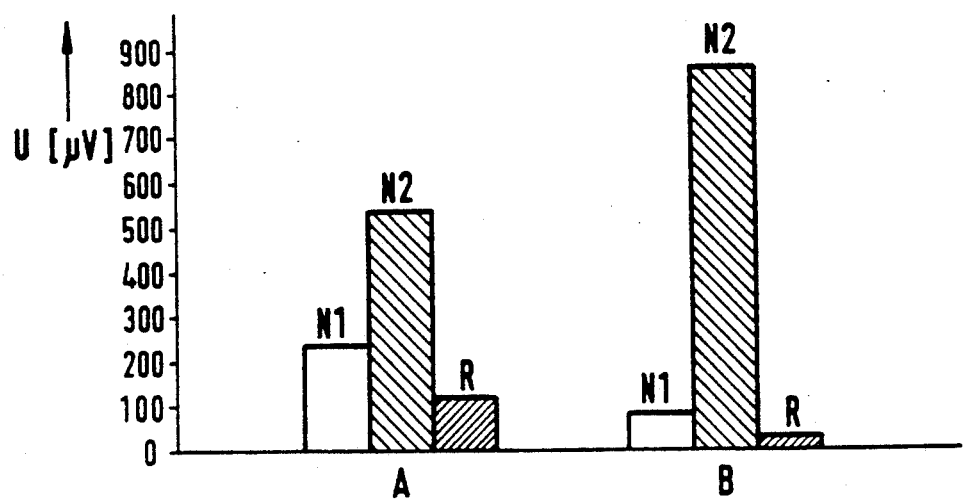
FIG. 5 is a diagram comparing the signal-to-noise ratio for the invention and for the prior art.

FIG. 5 shows the relationship between the useful signal and the noise for a capacitive liquid level detector A constructed according to prior art, compared with a liquid level detector B according to the invention. The noise signal R, the useful signal in the non-dipped-in state N1, and the useful signal in the dipped-in state N2 are respectively plotted thereon, the values for which were measured at the output of the differential amplifier 30. FIG. 5 shows that in the case of the construction according to the invention both the relationship of the useful signals N1, N2 to the noise signal R, and the difference between the useful signals N1 and N2, which is critical for the reliability of the detection, are significantly improved.

We claim:

1. A liquid transfer device for an analysis unit, the liquid transfer device comprising:
    a liquid transfer needle having a tip;
    a capacitive liquid level detector for detecting a dipping of the tip of the liquid transfer needle into an analysis liquid, the analysis liquid being contained in a vessel, said capacitive liquid level detector comprising
    a coaxial electrode arrangement including said liquid transfer needle and a first coaxial electrode coaxially surrounding said liquid transfer needle with the exception of the tip which projects therefrom, said first coaxial electrode being electrically insulated from said liquid transfer needle, wherein said liquid transfer needle and said first coaxial electrode of said coaxial electrode arrangement are coupled to a detection circuit comprising isolation amplifier circuit means for producing an output signal which corresponds to the input signal in phase and level, wherein an output side internal resistance of said isolation amplifier circuit means is lower than an input resistance thereof; said liquid level detector further comprising
    an a.c. voltage source connected to an input of said isolation amplifier circuit means and one of said first coaxial electrode and said liquid transfer needle, said one of the liquid transfer needle and said coaxial electrode forming a signal electrode,
    wherein the other of said liquid transfer needle and said first coaxial electrode is coupled to an output of said isolation amplifier circuit means and forms a compensating electrode.

2. A liquid transfer device according to claim 1, wherein said liquid transfer needle is connected to the input of said isolation amplifier circuit and said first coaxial electrode is connected to the output of the isolation amplifier circuit.

3. A liquid transfer device according to claim 1, wherein the coaxial electrode arrangement further comprises a second coaxial electrode which surrounds the signal electrode and the compensating electrode and is connected to a constant potential whereby it simultaneously forms a screening electrode and a counterelectrode of said capacitive liquid level detector.

4. A liquid transfer device according to claim 1 wherein the signal electrode is coupled to the a.c. voltage source through a load resistor.

5. A liquid transfer device according to claim 4, wherein said load resistor has a value which corresponds to an alternating current resistance of a useful capacitance at a selected frequency of the a.c. voltage source.

6. A liquid transfer device according to claim 5, wherein said detection circuit comprises a second isolation amplifier circuit means coupled to said a.c. voltage source, said detection circuit further comprising a differential amplifier connected to outputs of said first and second isolation amplifier circuit means, wherein said first isolation amplifier circuit means is identical to said second isolation amplifier circuit means.

7. A liquid transfer device according to claim 6, wherein said first and second isolation amplifier circuit means are integrated monolithically.

8. A liquid transfer device according to claim 1 further comprising electrical conductors connecting the coaxial electrode arrangement to the detection circuit, said electrical conductors comprising screened coaxial lines.

9. A liquid transfer device according to claim 8, further comprising hose means connected to said liquid transfer needle, said hose means for intaking and ejecting a liquid medium, said hose means including electrical screening.

10. A liquid transfer device for an analysis unit, the liquid transfer device comprising:
a liquid transfer needle having a tip;
a capacitive liquid level detector for detecting a dipping of the tip of the liquid transfer needle into an analysis liquid, the analysis liquid being contained in a vessel, said capacitive liquid level detector comprising
a coaxial electrode arrangement including said liquid transfer needle and at least two coaxial electrodes coaxially surrounding said liquid transfer needle with the exception of the tip which projects therefrom, said at least two coaxial electrodes being electrically insulated from said liquid transfer needle and from each other, wherein liquid transfer needle and said coaxial electrodes of said coaxial electrode arrangement are coupled to a detection circuit comprising isolation amplifier circuit means for producing an output signal which corresponds to the input signal in phase and level, wherein an output side internal resistance of said isolation amplifier circuit means is lower than an input resistance thereof; said liquid level detector further comprising
an a.c. voltage source connected to an input of said isolation amplifier circuit means and a first one of said at least two coaxial electrodes, said first one of said at least two coaxial electrodes forming a signal electrode,
wherein the other of said at least two coaxial electrodes is coupled to an output of said isolation amplifier circuit means and forms a compensating electrode.

11. A liquid transfer device according to claim 10, wherein the signal electrode is coupled to the a.c. voltage source through a high-value load resistor.

12. A liquid transfer device according to claim 11, wherein said load resistor has a value which corresponds to an alternating current resistance of a useful capacitance at a selected frequency of the a.c. voltage source.

13. A liquid transfer device according to claim 10, wherein said detection circuit comprises a second isolation amplifier circuit means coupled to said a.c. power source, said detection circuit further comprising a differential amplifier connected to outputs of said first and second isolation amplifier circuit means, wherein said first isolation amplifier circuit means is identical to said second isolation amplifier circuit means.

14. A liquid transfer device according to claim 13, wherein said first and second isolation amplifier circuit means are integrated monolithically.

15. A liquid transfer device according to claim 10, further comprising electrical conductors connecting the coaxial electrode arrangement to the detection circuit, said electrical conductors comprising screened coaxial lines.

16. A liquid transfer device according to claim 15, further comprising hose means connected to said liquid transfer needle, said hose means for intaking and ejecting a liquid medium, said hose means including electrical screening.

17. A liquid transfer device according to claim 10, wherein said coaxial electrode arrangement comprises at least three coaxial electrodes said signal electrode being arranged between two other electrodes of said coaxial electrode arrangement both of which are coupled to the output of said isolation amplifier circuit means and form compensating electrodes.

18. A liquid transfer device according to claim 17, wherein the signal electrode is coupled to the a.c. voltage source through a load resistor.

19. A liquid transfer device according to claim 18, wherein said load resistor has a value which corresponds to an alternating current resistance of a useful capacitance at a selected frequency of the a.c. voltage source.

20. A liquid transfer device according to claim 17, wherein said detection circuit comprises a second isolation amplifier circuit means coupled to said a.c. power source, said detection circuit further comprising a differential amplifier connected to outputs of said first and second isolation amplifier circuit means, wherein said first isolation amplifier circuit means is identical to said second isolation amplifier circuit means.

21. A liquid transfer device according to claim 20, wherein said first and second isolation amplifier circuit means are integrated monolithically.

22. A liquid transfer device according to claim 17, further comprising electrical conductors connecting the coaxial electrode arrangement to the detection circuit, said electrical conductors comprising screened coaxial lines.

23. A liquid transfer device according to claim 22, further comprising hose means connected to said liquid transfer needle, said hose means for intaking and ejecting a liquid medium, said hose means including electrical screening.

24. A method for detecting a level of liquid in a vessel of an analysis unit, said method comprising the steps of:
providing a liquid transfer device for an analysis unit, the liquid transfer device comprising a liquid transfer needle having a tip thereupon, and a capacitive liquid level detector for detecting a dipping of the tip of the liquid transfer needle into an analysis liquid, the analysis liquid being contained in a vessel, wherein the capacitive liquid level detector comprises a coaxial electrode arrangement including the liquid transfer needle and a first coaxial electrode coaxially surrounding the liquid transfer needle with the exception of the tip which projects therefrom, said first coaxial electrode being electrically insulated from said liquid transfer needle, wherein said liquid transfer needle and said first coaxial electrode of said coaxial electrode arrangement are coupled to a detection circuit comprising isolation amplifier circuit means for producing an output signal which corresponds to the input signal in phase and level, wherein an output side internal resistance of the isolation amplifier circuit means is lower than an input resistance thereof, with the liquid level detector further comprising an a.c.

voltage source connected to an input of the isolation amplifier circuit means and one of the first coaxial electrode and the liquid transfer needle, with the one of the liquid transfer needle and the coaxial electrode forming a signal electrode, wherein the other of the liquid transfer needle and the first coaxial electrode is coupled to an output of the isolation amplifier circuit means, and forms a compensating electrode; said method further comprising the steps of applying an input signal to said detection circuit and one of said liquid transfer needle and said first coaxial electrode;

applying an output signal of said detection circuit to another of said liquid transfer needle and said first coaxial electrode, thereby forming a stray field therebetween, said stray field forming a useful capacitance;

actively compensating other capacitance of the coaxial electrode arrangement; and measuring a change in voltage at an input of the isolation amplifier circuit means, said change in voltage being measured as a useful signal which is indicative of contacting of said liquid transfer needle to said analysis liquid.

* * * * *